(12) United States Patent
Matsufuji et al.

(10) Patent No.: US 8,147,931 B2
(45) Date of Patent: Apr. 3, 2012

(54) CELLULOSE-FILM MODIFIER, CELLULOSE COMPOSITION, AND OPTICAL CELLULOSE FILM, POLARIZING PLATE-PROTECTING FILM, POLARIZING PLATE, AND LIQUID CRYSTAL DISPLAY DEVICE, PRODUCED BY USING THE SAME

(75) Inventors: Akihiro Matsufuji, Minami-ashigara (JP); Takeichi Tatsuta, Minami-ashigara (JP); Yutaka Nozoe, Minami-ashigara (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 872 days.

(21) Appl. No.: 12/178,018

(22) Filed: Jul. 23, 2008

(65) Prior Publication Data

US 2009/0029073 A1 Jan. 29, 2009

(30) Foreign Application Priority Data

Jul. 25, 2007 (JP) .................. 2007-193896

(51) Int. Cl.
*C09K 17/32* (2006.01)
*G02F 1/1335* (2006.01)
*C08B 3/00* (2006.01)
*C08L 1/12* (2006.01)

(52) U.S. Cl. ......... 428/1.33; 349/117; 349/122; 536/58; 106/171.1

(58) Field of Classification Search .................. None
See application file for complete search history.

(56) References Cited

U.S. PATENT DOCUMENTS

2006/0232726 A1* 10/2006 Omatsu et al. .................. 349/96

FOREIGN PATENT DOCUMENTS

| JP | 9-095557 A | | 4/1997 |
|---|---|---|---|
| JP | 11-092574 A | * | 4/1999 |
| JP | 11-246704 A | | 9/1999 |
| JP | 2000-063560 A | | 2/2000 |
| JP | 2001-247717 A | | 9/2001 |
| JP | 2002-062430 A | | 2/2002 |
| JP | 2002-146044 A | | 5/2002 |
| JP | 2004-083589 A | | 3/2004 |
| JP | 2004-315613 A | | 11/2004 |
| JP | 2006-030937 A | | 2/2006 |
| WO | WO 95/27002 A1 | | 10/1995 |
| WO | WO 03/075880 A1 | * | 9/2003 |

OTHER PUBLICATIONS

Official Action issued on Nov. 15, 2011 in corresponding Japanese Patent Application No. 2007-193896, and an English language translation of the Official Action.

* cited by examiner

*Primary Examiner* — David Sample
*Assistant Examiner* — Nicole Gugliotta
(74) *Attorney, Agent, or Firm* — Buchanan Ingersoll & Rooney PC

(57) ABSTRACT

A cellulose-film modifier, having a compound represented by the following Formula (1):

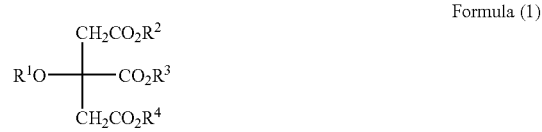

Formula (1)

wherein $R^1$ represents a hydrogen atom or an aliphatic or aromatic acyl group; $R^2$, $R^3$ and $R^4$ each represent a hydrogen atom or an aliphatic or aromatic group; and at least one of $R^2$, $R^3$ and $R^4$ represents an aliphatic group bonding via its secondary carbon; a cellulose composition, an optical cellulose film, a polarizing plate-protecting film, a polarizing plate, and a liquid crystal display device.

12 Claims, 1 Drawing Sheet

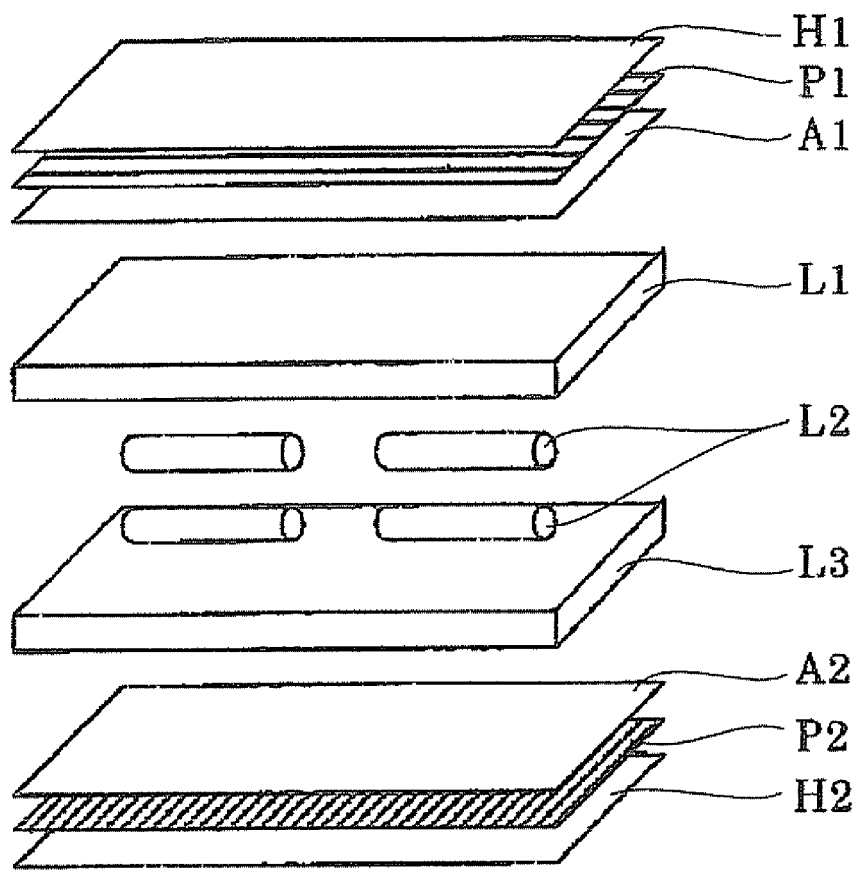

CELLULOSE-FILM MODIFIER, CELLULOSE COMPOSITION, AND OPTICAL CELLULOSE FILM, POLARIZING PLATE-PROTECTING FILM, POLARIZING PLATE, AND LIQUID CRYSTAL DISPLAY DEVICE, PRODUCED BY USING THE SAME

FIELD OF THE INVENTION

The present invention relates to a cellulose-film modifier, a cellulose composition, and an optical cellulose film, a polarizing plate-protecting film, a polarizing plate, and a liquid crystal display device that are produced by using the same. In particular, the present invention relates to a modifier for use in producing a cellulose film that is resistant to heat volatilization and to precipitation and is lower in optical anisotropy, an optical cellulose film produced by using the same, and a polarizing plate-protecting film, a polarizing plate, and a liquid crystal display device produced by using the cellulose film.

BACKGROUND OF THE INVENTION

Conventionally, cellulose acylate films, which are excellent in toughness and flame resistance, have been used as photographic substrates and various optical materials. In particular, recently, they are frequently used as optical transparent films for liquid crystal display devices. Cellulose acylate films, which are excellent in optical transparency and also in optical isotropy, are particularly advantageous as optical materials for use in devices handling polarized light such as liquid crystal display devices, and have been used as polarizer-protecting films and also as substrates for optical compensation films for widening view angle (view angle compensation).

A polarizing plate, a component of liquid crystal display device, has a polarizer and a polarizer-protecting film bonded to at least one side of the polarizer. Common polarizers are prepared by dyeing an oriented polyvinylalcohol (PVA)-based film with iodine or a dichroic dye. Frequently, a cellulose acylate film, in particular a triacetylcellulose film, that can be directly bonded to PVA is used as the polarizer-protecting film. The properties of the polarizing plate are significantly dependent on the optical properties of the polarizer-protecting film.

On the other hand, because cellulose acylate films generally show a moisture permeability drastically increased under high-temperature and high-humidity environment, leading to deterioration in properties, compared to other common substrates such as polyethylene terephthalate films, compounds called plasticizers are often added to the films. Typical examples of the plasticizers added to the cellulose acylate film include phosphoric triesters such as triphenyl phosphate and biphenyl diphenyl phosphate, phthalic esters, and the like (e.g., JP-A-9-95557 ("JP-A" means unexamined published Japanese patent application)). Other known examples thereof include sulfonamide compounds such as N-ethyl-toluenesulfonamide (e.g. JP-A-2004-315613), and it is known that increase in the plasticizer content leads to reduction of the moisture permeability and improvement of the film properties.

However, increase in the plasticizer content caused a problem of significant lowering of the glass transition point of the cellulose acylate film and deterioration in dimensional stability by film softening. In addition, simple increase in the addition amount of plasticizer unfavorably leads to incompatibility of the plasticizer with the cellulose acylate, and consequently to whitening of the resulting film and increase in optical anisotropy (e.g., retardation value in the thickness direction Rth). In addition, low-molecular weight plasticizers have high thermal volatility because of their low molecular weights, and they vaporize, for example, in the drying step during production. This problem has been considered as the major element involved in process contamination.

When a cellulose acylate film is used as an optical material, the optical anisotropy of the film is preferably lower in some applications. Among the so-called plasticizers described above, there are some compounds that are known to decrease the optical anisotropy of the cellulose acylate film, and fatty acid esters and amide compounds of particular polyvalent alcohols are disclosed as examples of such compounds (see e.g., JP-A-2001-247717, JP-A-2000-63560, JP-A-11-246704 and JP-A-2006-30937). However, increase in the addition amount of such a plasticizer often results in deterioration in compatibility thereof and causes whitening defects of the film. Further, there is a problem of process contamination caused by thermal volatilization during production. There is also a problem of elution of the plasticizer into the saponification solution used during processing of the polarizing plate.

For example, to solve the problems due to thermal volatility described above, known are methods of obtaining a cellulose acylate film lower in the moisture permeability by controlling the volatility by using polymeric compounds such as rosin resin, epoxy resin, ketone resin, or toluenesulfonamide resin (e.g., JP-A-2002-146044). However, the polymeric plasticizers are not sufficiently compatible with the cellulose acylate, and are not compatible as much as the low-molecular weight plasticizers.

Therefore, there exists an urgent need for development of a modifier that is favorably compatible with cellulose acylate, resistant to volatilization or precipitation during casting and drying, and resistant to elution into the saponification solution, and that gives a cellulose acylate film lower in optical anisotropy.

For example, citric esters were proposed as such (e.g., JP-A-11-092574), but they still had problems in that they are insufficient in lowering optical anisotropy and the dope stability was insufficient.

SUMMARY OF THE INVENTION

The present invention resides in a cellulose-film modifier, comprising a compound represented by the following Formula (1):

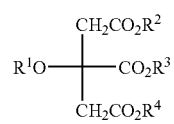

Formula (1)

wherein $R^1$ represents a hydrogen atom or an aliphatic or aromatic acyl group; $R^2$, $R^3$ and $R^4$ each represent a hydrogen atom or an aliphatic or aromatic group; and at least one of $R^2$, $R^3$ and $R^4$ represents an aliphatic group bonding via its secondary carbon.

The present invention also resides in a cellulose composition, containing a cellulose compound and at least one cellulose-film modifier.

The present invention also resides in an optical cellulose film, wherein at least one cellulose-film modifier is contained in a cellulose compound.

The present invention also resides in a polarizing plate-protecting film, having the optical cellulose film.

The present invention also resides in a polarizing plate having a polarization film and two transparent protective films placed on both sides of the polarization film, wherein at least one of the transparent protective films is the above described polarizing plate-protecting film.

The present invention also resides in a liquid crystal display device having a liquid crystal cell and two polarizing plates placed on both sides of the liquid crystal cell, wherein at least one of the polarizing plates is the above described polarizing plate.

Other and further features and advantages of the invention will appear more fully from the following description, appropriately referring to the accompanying drawings.

BRIEF DESCRIPTION OF THE DRAWING

FIG. 1 is a schematic view illustrating a favorable embodiment of the liquid crystal display device according to the present invention.

DETAILED DESCRIPTION OF THE INVENTION

According to the present invention, there is provided the following means:

(1) A cellulose-film modifier, comprising a compound represented by the following Formula (1):

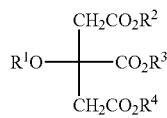

Formula (1)

wherein $R^1$ represents a hydrogen atom or an aliphatic or aromatic acyl group; $R^2$, $R^3$ and $R^4$ each represent a hydrogen atom or an aliphatic or aromatic group; and at least one of $R^2$, $R^3$ and $R^4$ represents an aliphatic group bonding via its secondary carbon (i.e. secondary carbon atom).

(2) The cellulose-film modifier described in item (1), wherein the compound represented by Formula (1) is a compound represented by the following Formula (2):

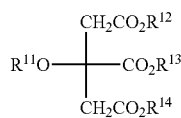

Formula (2)

wherein $R^{11}$ represents a hydrogen atom or an aliphatic acyl group; $R^{12}$, $R^{13}$ and $R^{14}$ each represent an aliphatic group; and at least one of $R^{12}$, $R^{13}$ and $R^{14}$ represents an aliphatic group bonding via its secondary carbon.

(3) The cellulose-film modifier described in item (1), wherein the compound represented by Formula (1) is a compound represented by the following Formula (3):

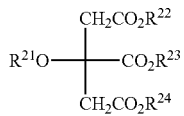

Formula (3)

wherein $R^{21}$ represents a hydrogen atom or an aliphatic acyl group; $R^{22}$, $R^{23}$ and $R^{24}$ each represent a hydrogen atom or an aliphatic group having a branched or cyclic structure; and at least one of $R^{22}$, $R^{23}$ and $R^{24}$ represents an aliphatic group bonding via its secondary carbon.

(4) A cellulose composition, containing a cellulose compound and at least one cellulose-film modifier described in any one of items (1) to (3).

(5) An optical cellulose film, wherein at least one cellulose-film modifier described in any one of items (1) to (3) is contained in a cellulose compound.

(6) The optical cellulose film described in item (5), wherein the cellulose compound contained in the cellulose film is a cellulose acylate.

(7) The optical cellulose film described in item (6), wherein the acyl substitution degree of the cellulose acylate is 2.60 to 3.00.

(8) The optical cellulose film described in any one of items (5) to (7), wherein the substitution degree of acyl groups having 3 to 22 carbon atoms in the cellulose acylate is 0.00 to 0.80.

(9) The optical cellulose film described in any one of items (5) to (8), wherein Re value at a wavelength of 590 nm is 0 nm or more and 20 nm or less, and Rth value at a wavelength of 590 nm is −10 nm or more and 15 nm or less.

(10) The optical cellulose film described in any one of items (5) to (8), wherein the Rth values at wavelengths of 480 nm and 630 nm satisfy the relationship shown by the following mathematical formula (1):

|Rth(630)−Rth(480)|≦20.    Mathematical formula (1)

(11) The optical cellulose film described in any one of items (5) to (10), containing the cellulose compound and at least one compound represented by any one of the Formulae (1) to (3) in an amount of 2 to 30 mass % of the cellulose compound.

(12) A polarizing plate-protecting film, having the optical cellulose film described in any one of items (5) to (10).

(13) A polarizing plate, having a polarization film and two transparent protective films placed on both sides of the polarization film, wherein at least one of the transparent protective films is the polarizing plate-protecting film described in item (12).

(14) A liquid crystal display device, having a liquid crystal cell and two polarizing plates placed on both sides of the liquid crystal cell, wherein at least one of the polarizing plates is the polarizing plate described in item (13).

(15) A silver halide photographic photosensitive material, having the cellulose film described in any one of items (5) to (10).

Hereinafter, the present invention will be described in detail. The constitutional requirements described below may be embodied on the basis of the representative embodiments of the present invention. However the present invention is not limited to such embodiments.

In the present specification, "to" denotes a range including numerical values described before and after it as a minimum value and a maximum value.

The cellulose composition according to the present invention is a composition comprising a cellulose compound or comprising a cellulosic skeleton-containing compound (cellulosic derivative) obtained from a raw cellulose material by introducing functional groups thereto biologically or chemically. Among the cellulose compounds, cellulose esters are preferable, and cellulose acylates are more preferable.

[Cellulose-Film Modifier]

In the present invention, at least one of the compounds represented by Formula (1) is used as a cellulose-film modifier (dope stabilizer or retardation-controlling agent).

Hereinafter, the compound represented by Formula (1) according to the present invention will be described.

The compound represented by Formula (1) is a succinic ester, wherein $R^1$ represents a hydrogen atom, a substituted or unsubstituted aliphatic acyl group, or a substituted or unsubstituted aromatic acyl group; preferably a hydrogen atom or an aliphatic acyl group. The aliphatic acyl group may be linear, branched, or cyclic. The carbon atom number of the aliphatic acyl group is preferably 1 to 12, more preferably 1 to 8, and most preferably 1 to 4. The aromatic acyl group may be an aromatic hydrocarbon acyl group or an aromatic heterocyclic acyl group, and is more preferably an aromatic hydrocarbon acyl group. Among the aromatic hydrocarbon acyl groups, those having 6 to 24 carbon atoms are preferable, and those having 6 to 12 carbon atoms are more preferable. The substituents which the aliphatic and aromatic acyl groups may have include the substituent T described below.

$R^2$, $R^3$ and $R^4$ each represent a hydrogen atom, a substituted or unsubstituted aliphatic group or a substituted or unsubstituted aromatic group, more preferably an aliphatic group. The aliphatic group may be a linear, branched, or cyclic group, and is more preferably a branched or cyclic group and particularly preferably a cyclic group. However, at least one, preferably two, and more preferably all of $R^2$, $R^3$ and $R^4$ are aliphatic groups bonding via secondary carbons. The carbon atom number of the aliphatic group is preferably 5 to 24, more preferably 5 to 15, and most preferably 5 to 12. The aromatic group may be an aromatic hydrocarbon group or an aromatic heterocyclic group, more preferably an aromatic hydrocarbon group. The aromatic hydrocarbon group is preferably a group having 6 to 24 carbon atoms, more preferably a group having 6 to 12 carbon atoms. Examples of the substituents which the aliphatic and aromatic groups may have include the substituents T described below.

The compound represented by Formula (1) is preferably a compound represented by Formula (2).

In Formula (2), $R^{11}$ represents a hydrogen atom or a substituted or unsubstituted aliphatic acyl group, preferably a hydrogen atom or an unsubstituted aliphatic acyl group. The aliphatic acyl group may be a linear, branched, or cyclic group. The carbon atom number of the aliphatic acyl group is preferably 1 to 12, more preferably 1 to 8, and most preferably 1 to 4. $R^{12}$, $R^{13}$ and $R^{14}$ each represent a hydrogen atom or a substituted or unsubstituted aliphatic group, preferably an aliphatic group. The aliphatic group may be a linear, branched, or cyclic group; and is more preferably a branched or cyclic group and particularly preferably a cyclic group. However, at least one, preferably two, and more preferably all of $R^{12}$, $R^{13}$ and $R^{14}$ are aliphatic groups bonding via secondary carbon. The carbon atom number of the aliphatic group is preferably 5 to 24, more preferably 5 to 15 and most preferably 5 to 12.

The compound represented by Formula (1) is more preferably a compound represented by Formula (3).

In Formula (3), $R^{21}$ represents a hydrogen atom or a substituted or unsubstituted aliphatic acyl group. The aliphatic acyl group may be a linear, branched, or cyclic group. The carbon atom number of the aliphatic acyl group is preferably 1 to 12, more preferably 1 to 8 and most preferably 1 to 4. $R^{22}$, $R^{23}$ and $R^{24}$ each represent a hydrogen atom or an aliphatic group having a branched or cyclic structure. However, at least one, preferably two, and more preferably all of $R^{22}$, $R^{23}$ and $R^{24}$ are aliphatic groups bonding via secondary carbons. Examples of the aliphatic group bonding via its secondary carbon include 1-ethylpropyl, 1-ethylbutyl, 1-propylbutyl, 1-methyl-3-butenyl, 1,3-dimethylbutyl, 1-methylhexyl, 1-phenylheptyl, 1-methylpropyl, 1-methylnonenyl, cyclohexyl,

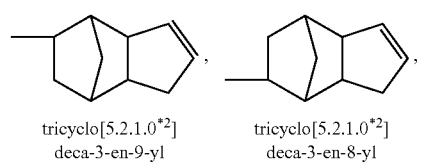

tricyclo[5.2.1.0*²]  tricyclo[5.2.1.0*²]
deca-3-en-9-yl   deca-3-en-8-yl 1,3-dimethylbutyl, and the like.

The carbon atom number of the aliphatic group is preferably 5 to 24, more preferably 5 to 15, and most preferably 5 to 12.

Hereinafter, the substituted or unsubstituted aliphatic acyl group described above will be explained. The aliphatic acyl group may be a linear, branched, or cyclic group. Typical examples of the aliphatic acyl group include acetyl, propionyl, butyryl, isobutyryl, valeryl, isovaleryl, trimethylacetyl, 2-methylbutyryl, hexanoyl, 2-ethylbutyryl, 2,2-dimethylbutyryl, t-butylacetyl, 2-methylvaleryl, 3-methylvaleryl, 4-methylvaleryl, heptanoyl, 2-methylhexanoyl, octanoyl, 2-propylpentanoyl, 2-ethylhexanoyl, nonanoyl, decanoyl, undecanoyl, and lauryl groups, and the like; more preferable are acetyl, propionyl, and butyryl groups; and still more preferable is an acetyl group.

Hereinafter, the substituted or unsubstituted aromatic acyl group described above will be explained. Typical examples of the aromatic acyl group include benzoyl, 1-naphthoyl, and 2-naphthoyl groups, and the like, and preferable is a benzoyl group.

Hereinafter, the substituted or unsubstituted aliphatic group described above will be explained. The aliphatic group may be a linear, branched, or cyclic group; those having 5 to 24 carbon atoms are preferable; those having 5 to 15 carbon atoms are more preferable; and those having 5 to 12 carbon atoms are particularly preferable. Typical examples of the aliphatic group include amyl, isoamyl, tert-amyl, n-hexyl, cyclohexyl, n-heptyl, n-octyl, bicyclooctyl, adamantyl, n-decyl, tert-octyl, dodecyl, hexadecyl, octadecyl, and didecyl groups, and the like.

Hereinafter, the aromatic group described above will be explained. The aromatic group may be an aromatic hydrocarbon group or an aromatic heterocyclic group and is more preferably an aromatic hydrocarbon group. As the aromatic hydrocarbon group, aromatic hydrocarbon groups having 6 to 24 carbon atoms are preferable, and those having 6 to 12 carbon atoms are more preferable. Typical examples of the rings of the aromatic hydrocarbon group include benzene, naphthalene, anthracene, biphenyl, terphenyl, and the like. The aromatic hydrocarbon group is particularly preferably benzene, naphthalene, or biphenyl. The aromatic heterocyclic group is preferably a group having at least one of oxygen, nitrogen, and sulfur atoms. Typical examples of the heterocycle include furan, pyrrole, thiophene, imidazole, pyrazole, pyridine, pyrazine, pyridazine, triazole, triazine, indole, indazole, purine, thiazoline, thiadiazole, oxazoline, oxazole, oxadiazole, quinoline, isoquinoline, phthalazine, naphthyridine, quinoxaline, quinazoline, cinnoline, pteridine, acridine, phenantroline, phenazine, tetrazole, benzimidazole, benzoxazole, benzothiazole, benzotriazole, tetrazaindene, and the like. Particularly favorable aromatic heterocyclic groups are pyridine, triazine, and quinoline.

Hereinafter, the substituent T described above will be described in detail.

Examples of the substituent T include alkyl groups (preferably having 1 to 20 carbon atoms, more preferably 1 to 12, and particularly preferably 1 to 8, such as methyl, ethyl, isopropyl, tert-butyl, n-octyl, n-decyl, n-hexadecyl, cyclopropyl, cyclopentyl and cyclohexyl groups, and the like), alkenyl groups (preferably having 2 to 20 carbon atoms, more preferably 2 to 12, and particularly preferably 2 to 8, such as vinyl, allyl, 2-butenyl and 3-pentenyl groups, and the like), alkynyl groups (preferably having 2 to 20 carbon atoms, more preferably 2 to 12, and particularly preferably 2 to 8, such as propargyl and 3-pentynyl groups, and the like), aryl groups (preferably having 6 to 30 carbon atoms, more preferably 6 to 20, and particularly preferably 6 to 12, such as phenyl, biphenyl and naphthyl groups and the like), substituted or unsubstituted amino groups (preferably having 0 to 20 carbon atoms, more preferably 0 to 10, and particularly preferably 0 to 6, such as amino, methylamino, dimethylamino, diethylamino and dibenzylamino groups and the like), alkoxy groups (preferably having 1 to 20 carbon atoms, more preferably 1 to 12, and particularly preferably 1 to 8, such as methoxy, ethoxy and butoxy groups and the like), aryloxy groups (preferably having 6 to 20 carbon atoms, more preferably 6 to 16, and particularly preferably 6 to 12, such as phenyloxy and 2-naphthyloxy groups and the like), acyl groups (preferably having 1 to 20 carbon atoms, more preferably 1 to 16, and particularly preferably 1 to 12, such as acetyl, benzoyl, formyl and pivaloyl groups and the like), alkoxycarbonyl groups (preferably having 2 to 20 carbon atoms, more preferably 2 to 16, and particularly preferably 2 to 12, such as methoxycarbonyl and ethoxycarbonyl groups and the like), aryloxycarbonyl groups (preferably having 7 to 20 carbon atoms, more preferably 7 to 16, and particularly preferably 7 to 10, such as phenyloxycarbonyl group and the like), acyloxy groups (preferably having 2 to 20 carbon atoms, more preferably 2 to 16, and particularly preferably 2 to 10, such as acetoxy and benzoyloxy groups and the like), acylamino groups (preferably having 2 to 20 carbon atoms, more preferably 2 to 16, and particularly preferably 2 to 10, such as acetylamino and benzoylamino groups, and the like), alkoxycarbonylamino groups (preferably having 2 to 20 carbon atoms, more preferably 2 to 16, and particularly preferably 2 to 12, such as methoxycarbonylamino group and the like), aryloxycarbonylamino groups (preferably having 7 to 20 carbon atoms, more preferably 7 to 16, and particularly preferably 7 to 12, such as phenyloxycarbonylamino group and the like), sulfonylamino groups (preferably having 1 to 20 carbon atoms, more preferably 1 to 16, and particularly preferably 1 to 12, such as methanesulfonylamino and benzenesulfonylamino groups, and the like), sulfamoyl groups (preferably having 0 to 20 carbon atoms, more preferably 0 to 16, and particularly preferably 0 to 12, such as sulfamoyl, methylsulfamoyl, dimethylsulfamoyl and phenylsulfamoyl groups, and the like), carbamoyl groups (preferably having 1 to 20 carbon atoms, more preferably 1 to 16, and particularly preferably 1 to 12, such as carbamoyl, methylcarbamoyl, diethylcarbamoyl and phenylcarbamoyl groups, and the like), alkylthio groups (preferably having 1 to 20 carbon atoms, more preferably 1 to 16, and particularly preferably 1 to 12, such as methylthio and ethylthio groups and the like), arylthio groups (preferably having 6 to 20 carbon atoms, more preferably 6 to 16, and particularly preferably 6 to 12, such as phenylthio group and the like), sulfonyl groups (preferably having 1 to 20 carbon atoms, more preferably 1 to 16, and particularly preferably 1 to 12, such as mesyl and tosyl groups and the like), sulfinyl groups (preferably having 1 to 20 carbon atoms, more preferably 1 to 16, and particularly preferably 1 to 12, such as methanesulfinyl and benzenesulfinyl groups, and the like), ureido groups (preferably having 1 to 20 carbon atoms, more preferably 1 to 16, and particularly preferably 1 to 12, such as ureido, methylureido and phenylureido groups, and the like), phosphoramido groups (preferably having 1 to 20 carbon atoms, more preferably 1 to 16, and particularly preferably 1 to 12, such as diethylphosphoramido and phenylphosphoramido groups and the like), a hydroxy group, a mercapto group, halogen atoms (e.g., fluorine atom, chlorine atom, bromine atom, iodine atom), a cyano group, a sulfo group, a carboxyl group, a nitro group, a hydroxamic acid group, a sulfino group, a hydrazino group, an imino group, heterocyclic groups (preferably having 1 to 30 carbon atoms, more preferably 1 to 12, and having one or more heteroatoms such as of nitrogen, oxygen, and sulfur, such as irmidazolyl, pyridyl, quinolyl, furyl, pyperidyl, morpholino, benzoxazolyl, benzimidazolyl and benzothiazolyl groups and the like), silyl groups (preferably, having 3 to 40 carbon atoms, more preferably 3 to 30, and particularly preferably 3 to 24, such as trimethylsilyl, triphenylsilyl groups and the like), and others.

These substituents may further be substituted. If two or more substituents are present, the substituents may be the same as or different from each other. Alternatively, they may bind to each other, forming a ring, if possible.

Herein, in the present specification, the $Re(\lambda)$ and the $Rth(\lambda)$ indicate the in-plane retardation and the retardation in the direction of the thickness, respectively, at the wavelength $\lambda$ (nm). The $Re(\lambda)$ can be measured by making light of wavelength $\lambda$ nm incident in the direction of the normal of the film, in KOBRA 21 ADH or WR (each trade name, manufactured by Oji Scientific Instruments).

In the case where the film to be measured can be expressed by a uniaxial or biaxial index ellipsoid (polarizability ellipsoid), the $Rth(\lambda)$ thereof is calculated as follows.

$Rth(\lambda)$ is calculated using KOBRA 21ADH or WR on the basis of: the above-described $Re(\lambda)$; retardation values in total six directions measured by making light of wavelength $\lambda$ nm incident in the normal direction and directions inclined to 50° at an interval of 10° over the normal direction of the film with the in-plane retardation axis (judged by the KOBRA 21 ADH or WR) as an inclined axis (a rotation axis) (or with an arbitrary direction in the film plane as a rotation axis when there is no retardation axis); the estimated average refractive index; and, the input value of the film thickness.

In the above-described method, when the film has a retardation value of zero in a direction inclined to a certain degree over the normal direction with the in-plane retardation axis as a rotation axis, the retardation value in a direction inclined to a larger degree than the above-described direction is calculated by KOBRA 21ADH or WR, after the sign of the retardation value is converted to negative.

Alternatively, Rth may also be calculated by mathematical formulae (2) and (3), on the basis of: retardation values measured from arbitrary inclined two directions, with the retardation axis as an inclined axis (a rotation axis) (or with the in-plane arbitrary direction as a rotation axis when there is no retardation axis); the estimated average refractive index; and the input value of the film thickness.

$$Re(\theta) = \left[ nx - \frac{ny \times nz}{\sqrt{\left\{ny\sin\left(\sin^{-1}\left(\frac{\sin(-\theta)}{nx}\right)\right)\right\}^2 + \left\{nz\cos\left(\sin^{-1}\left(\frac{\sin(-\theta)}{nx}\right)\right)\right\}^2}}\right] \times \frac{d}{\cos\left(\sin^{-1}\left(\frac{\sin(-\theta)}{nx}\right)\right)}$$

Mathematical formula (2)

Note:

The above $Re(\theta)$ represents a retardation value in the direction inclined by an angle $\theta$ from the normal direction. In the mathematical formula (2), nx represents a refractive index in the retardation axis direction in the plane, ny represents a refractive index in the direction orthogonal to nx in the plane, and nz represents a refractive index in the direction orthogonal to nx and ny. d represents film thickness.

$$Rth=((nx+ny)/2-nz)\times d$$ mathematical formula (3)

In the case where the film to be measured cannot be expressed by a uniaxial or biaxial index ellipsoid, i.e. a film having no so-called optic axis, the $Rth(\lambda)$ thereof is calculated as follows.

$Rth(\lambda)$ is calculated using KOBRA 21 ADH or WR, on the basis of: the above-described $Re(\lambda)$; retardation values measured in eleven directions, by making light of wavelength $\lambda$ nm incident in the directions inclined to −50° to +50° at an interval of 10° over the normal direction of the film with the in-plane retardation axis (judged by the KOBRA 21ADH or WR) as an inclined axis (a rotation axis); the estimated average refractive index; and the input value of the film thickness.

In the above measurement methods, as the estimated (hypothetical) value of the average refractive index, use may be made, for example, of values described in "Polymer Handbook" (JOHN WILEY & SONS, INC.) and values described in catalogues of various optical films. For films whose average refractive indexes are unknown, the values may be measured to determine by an Abbe refractometer. Average refractive indexes of major optical films are exemplified in below: cellulose acetate (1.48), cycloolefin polymer (1.52), polycarbonate (1.59), polymethyl methacrylate (1.49), and polystyrene (1.59). KOBRA21ADH or WR can calculate nx, ny, and nz, by inputting these estimated values of the average refractive index and the film thickness. From the thus-calculated nx, ny, and nz, Nz=(nx−nz)/(nx−ny) is further calculated.

In particular, among the compounds represented by Formulae (1) to (3), the secondary alcohol esters represented by Formula (4) are favorable, because the ester groups in such compounds are less subject to hydrolysis:

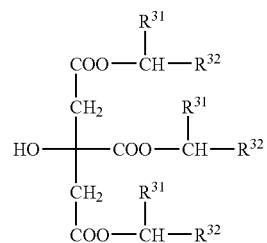

Formula (4)

In formula (4), $R^{31}$ and $R^{32}$ each represent an aliphatic group, and typical examples thereof are selected appropriately from those described for Formulae (1) to (3). $R^{31}$ and $R^{32}$ may be the same as or different from each other.

The molecular weight of the compound represented by any one of Formulae (1) to (4) is preferably 350 or more, more preferably 400 or more. Increase of molecular weight, i.e., increase in bulkiness of the $R^2$ hydrocarbon group in Formula (1), may lead to increase in hydrophobicity, which in turn leads to deterioration in compatibility with cellulose acylate. The molecular weight is preferably 550 or less, more preferably 500 or less.

The addition amount of the compound represented by Formula (1) to (4) is preferably 1 to 30 mass %, more preferably 2 to 25 mass %, and most preferably 3 to 20 mass %, with respect to the cellulose compound.

Favorable examples of the compounds represented by Formula (1) to (4) will be shown below, by taking the compound shown in Formula (1) as an example, but it should be understood that the present invention is not limited to these typical examples. For example, in the following Formula, compounds wherein $R^2$, $R^3$ and R4 are the same are easier to produce, but those in Table 1 wherein $R^2$, $R^3$, $R^4$ are different from each other may be used.

TABLE 1

| Compound | $R^1$ | $R^2, R^3, R^4$ |
|---|---|---|
| A-1 | H | —CH($C_2H_5$)$_2$ |
| A-2 | H | —CH($C_2H_5$)($C_3H_7$) |
| A-3 | H | —CH(($CH_2$)$_2$$CH_3$)$_2$ |
| A-4 | H | —CH($CH_3$)$CH_2$CH=$CH_2$ |
| A-5 | H | —CH($CH_3$)($CH_2$CH($CH_3$)$_2$) |
| A-6 | H | —CH($CH_3$)($C_5H_{11}$) |
| A-7 | H | —CH($C_6H_5$)($C_6H_{13}$) |
| A-8 | H | —CH($CH_3$)($C_2H_5$) |
| A-9 | H | —CH($CH_3$)($C_8H_{15}$) |
| A-10 | H | ⬡ |
| A-11 | H | (bicyclic structures) Note 1) |
| A-12 | $CH_3CO$ | —CH($CH_3$)($CH_2$CH($CH_3$)$_2$) |

Note 1)
These two groups are present as mixed in $R^2$, $R^3$, and $R^4$.

[Composition]

The composition according to the present invention is a composition containing at least one of the compounds represented by Formulae (1) to (4) according to the present invention and a cellulose compound, preferably a cellulose acylate.

In another embodiment of the present invention, provided is a film prepared by using the composition above. The composition according to the present invention is not particularly limited in state, and may be liquid (e.g., solution containing cellulose acylate) or solid (e.g., film containing cellulose acylate as the primary raw material).

The cellulose acylates, typical examples of the cellulose compounds for use in the present invention, will be described below in detail.

<Cellulose Acylate Raw Cotton>

Examples of the cellulose of the cellulose acylate raw material that can be used in the present invention include cotton linter and wood pulp (broadleaf pulp, and conifer (needle leaf) pulp). Any cellulose obtained from any raw cellulose may be used, and a plurality of celluloses may be used in combination of two or more thereof according to the need. There are detailed descriptions of these raw celluloses in, for example, "Plastic Material Lectures (17) Cellulose Resin" (Marusawa and Uda, The Nikkan Kogyo Shimbun, Ltd., published in 1970); and Japan Institute of Invention and Innovation, Kokai Giho (Open Technical Report) 2001-1745 (pp. 7 to 8), and the raw celluloses described in these publications may be used in the present invention, but these examples are not intended to be limiting of the cellulose acylate that can be used in the invention.

The aforementioned specific cellulose acylate is preferably a mixed fatty acid ester of a cellulose obtained by substituting a hydroxyl group of the cellulose with an acetyl group and a cellulose obtained by substituting a hydroxyl group with an acyl group having 3 or more carbon atoms, in which degree of substitution for a hydroxyl group per glucose unit of the cellulose satisfies the following mathematical formulae (4) and (5).

$$2.0 \leq A+B \leq 3.0 \qquad \text{Mathematical formula (4)}$$

$$0 \leq B \qquad \text{Mathematical formula (5)}$$

Herein, A represents the degree of substitution of an acetyl group substituting for a hydroxyl group of the cellulose, and B represents the degree of substitution of an acyl group having 3 or more carbon atoms substituting for a hydroxyl group of the cellulose.

The substitution degree of the cellulose acetate (when B is 0) is preferably 2.5 or more, more preferably 2.8 or more, and still more preferably 2.9 or more.

<Degree of Polymerization of Cellulose Acylate>

The degree of polymerization of cellulose acylate that can be used in the present invention is preferably 180 to 700 in terms of viscosity average degree of polymerization. In the case of cellulose acetate, the degree of polymerization is preferably 180 to 550, more preferably 180 to 400, and particularly preferably 180 to 350, in terms of viscosity average degree of polymerization. By adjusting the degree of polymerization to 700 or less, the viscosity of a dope solution of cellulose acylate becomes an adequate one and the production of a film by flow casting then tends to be facilitated. In addition, adjusting the degree of polymerization to 180 or more is preferable because the strength of a film formed can be further increased. The average polymerization degree can be measured by a limiting viscosity method by Uda et ale, (Kazuo Uda and Hideo Saito, "The Journal of the Society of Fiber Science and Technology, Japan", Vol. 18, No. 1, pp. 105 to 120, 1962). Specifically, it can be determined according to the method described in JP-A-9-95538.

Further, the distribution of molecular weight of a cellulose acylate that can be used in the present invention is evaluated by gel permeation chromatography. The polydisperse index Mw/Mn (Mw, mass average molecular weight; and Mn, number average molecular weight) is preferably from 1.0 to 4.0, more preferably from 2.0 to 3.0.

About the cellulose acylate that can be used in the present invention, the starting cotton thereof, and the synthesis method thereof are described in detail in, for example, "Kokai Giho" by Japan Institute of Invention & Innovation (Kogi No. 2001-1745, published on Mar. 15, 2001), pp. 7 to 12, and they can be applied to the present invention.

<Additive to Cellulose Acylate>

To a cellulose acylate solution that can be used in the present invention, in addition to the compound represented by formula (1), any of various additives (for example, an optical-characteristic controlling agent, a ultraviolet absorber, a plasticizer, a deterioration preventing agent, and fine particles) may be added. As to the timing at which the compound represented by formula (1) and the other additive(s) is added, they may be added in any of the dope production steps. They may be added in the last step (as a control step) of the dope preparation steps.

The additive(s) may be in a solid or oily state. That is, there is no particular limitation to the melting points or boiling points of the additives. Specifically, the method described in JP-A-2001-151901 can be applied to the present invention.

[Optical-Characteristic Controlling Agent]

It is possible to reduce Rth of the film by addition of the polymer additives. However, the Rth of the cellulose acylate may vary according to the wavelength, and the values at the longer wavelength and shorter wavelength can differ significantly. Thus, the Rth values at wavelengths of 480 nm and 650 nm preferably have a relationship satisfying the following mathematical formula (6).

$$|Rth(630)-Rth(480)| \leq 20 \qquad \text{Mathematical formula (6)}$$

In order to satisfy the relationship, it is preferable to use additionally a compound capable of modifying the wavelength dispersion of optical properties.

The wavelength dispersion-modifying compound is preferably a compound having benzotriazole, benzophenone, cyanoacrylate, or triazine as a main skeleton, which may further be substituted with various substituents. Favorable examples thereof are shown below, but are not limited thereto. In the following formulae, R. represents an organic substituent, and $R^1$ represents H, OH or an organic substituent. The organic substituent is, for example, an alkyl group having 1 to 12 carbon atoms, an allyl group, or the like. These compounds preferably have the absorption maximum in the UV region of 200 to 400 nm, and preferably no absorption in the visible region for colorlessness.

Compound 3

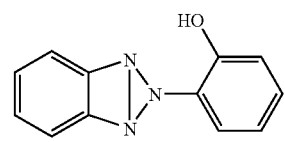

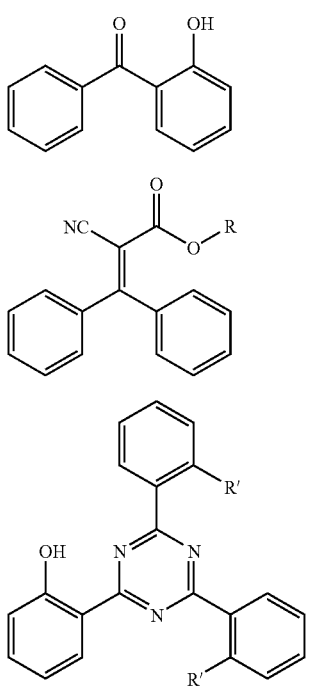

Compound 4

Compound 5

Compound 6

Examples of the compound 3 include 2-(2-hydroxy-5-t-octylphenyl)-2H-benzotriazole, 2-(2-hydroxy-5-methylphenyl)-2H-benzotriazole, 2-(2-hydroxy-5-methylphenyl)-2H-benzotriazole, 2-(2-hydroxy-5-t-butylphenyl)-2H-benzotriazole, 2-(2-hydroxy-3-t-butyl-5-methylphenyl)-2H-benzotriazole, 2-(2-hydroxy-3,5-di-t-butylphenyl)-2H-benzotriazole, 2-(2-hydroxy-3,5-di-t-pentylphenyl)-2H-benzotriazole, 2-[2-hydroxy-3-(3,4,5,6-tetrahydrophthalamido-methyl)-5-methylphenyl] benzotriazole, esters of benzene propanoic acid-3-(2H-benzotriazol-2-yl)-5-(1,1-dimethylethyl)-4-hydroxy with a C7-9 branched- or straight-chain alkyl; 2-(2-hydroxy-3,5-bis (1-methyl-1-phenylethyl)phenyl)-2H-benzotriazole, and the like.

Examples of the compound 4 include 2-hydroxy-4-n-hectoxybenzophenone, 2-hydroxy-4-n-octoxybenzophenone, 2-hydroxy-4-benzyloxybenzophenone, 2,2'-dihydroxy-4,4'-dimethoxybenzophenone, 2,2'-dihydroxy-4-methoxybenzophenone, and the like.

Examples of the compound 5 include ethyl-2-cyano-3,3-diphenyl acrylate, (2-ethylhexyl)-2-cyano-3,3-diphenyl acrylate, decyl-2-cyano-3-(5-methoxy-phenyl) acrylate, and the like.

Examples of the compound 6 include 2,4-bis(2-hydroxy-4-butoxyphenyl)-6-(2,4-dibutoxyphenyl)-1,3-5-triazine, 2-(2,4-dihydroxyphenyl)-4,6-bis-(2,4-dimethylphenyl)-1,3,5-triazine, 2-(2-hydroxy-4-butoxyphenyl)-4,6-diphenyl-1,3,5-triazine, and the like.

Examples of the other compounds include salicylate esters such as phenyl salicylate and tolyl salicylate, esters such as (2,4-di-t-butyl)phenyl-(4-hydroxy-3,5-di-t-butyl) benzoate, and the like.

Benzotriazole-, benzophenone-, and triazine-based compounds are more preferable.

It is possible to adjust the wavelength dispersion of the Rth of optical film, by adding at least one of the compounds capable of modifying the wavelength dispersion of optical properties in an amount of 0.1 to 30 mass %, more preferably 0.2 to 10 mass %, and still more preferably 0.5 to 2 mass %, with respect to 100 mass % of the cellulose acylate. The addition amount is preferably in the range above, from the viewpoints of absorption in the visible range (coloring) and the value |Rth(630)−Rth(480)|.

(Ultraviolet Absorber)

Any kind of ultraviolet absorber can be selected according to the purpose of use, and examples of the UV absorber that can be used include those of salicylate ester-series, benzophenone-series, benzotriazole-series, triazine-series, benzoate-series, cyanoacrylate-series, and nickel complex-series; and a benzophenone-series, benzotriazole-series, or salicylate ester-series UV absorber is preferable.

The optical-characteristic controlling agent described above, which absorbs the light in the ultraviolet range, can also serve as an ultraviolet absorbent.

It is preferable to use two or more ultraviolet absorbers having different absorption wavelength in combination, because great shielding ability can be obtained in a wide wavelength range. As the ultraviolet absorber for liquid crystal, preferable one is a ultraviolet absorber which is excellent in absorption ability for ultraviolet ray of wavelength 370 nm or lower, from the viewpoint of prevention of degradation of the liquid crystal, and which has less absorption of visible light of wavelength 400 nm or higher, from the viewpoint of displaying ability of the liquid crystal. Examples of the particularly preferable ultraviolet absorber include the aforementioned benzotriazole-series compounds, benzophenone-series compounds, and salicylate ester-series compounds. Among these, benzotriazole-series compounds are especially preferable, because of little coloration which is unnecessary against cellulose ester.

Further, as the UV absorber, use can also be made of any of the compounds described in JP-A-60-235852, JP-A-3-199201, JP-A-5-1907073, JP-A-5-194789, JP-A-5-271471, JP-A-6-107854, JP-A-6-118233, JP-A-6-148430, JP-A-7-11056, JP-A-7-11055, JP-A-7-11056, JP-A-8-29619, JP-A-8-239509, and JP-A-2000-204173.

The amount of the ultraviolet absorber to be added is preferably 0.001 to 5 mass %, more preferably 0.01 to 1 mass %, to the cellulose acylate. When the amount to be added is not less than 0.001 mass %, the addition effect can be sufficiently exhibited, which is preferable, and when the amount to be added is not more than 5 mass %, the ultraviolet absorber can be prohibited from being bleed out on the film surface, which is preferable.

Further, the ultraviolet absorber may be added at the same time upon dissolving a cellulose acylate, or may be added into the cellulose acylate solution (dope) after dissolution. It is particularly preferred that an ultraviolet absorber solution is added to the dope immediately before casting, by means of a static mixer or the like, thereby optical absorption characteristics can be easily controlled.

(Deterioration Preventing Agent)

The deterioration preventing agent may be added to prevent cellulose triacetate etc. from its degradation and decomposition. As the deterioration preventing agent, butyl amine, hindered amine compounds (JP-A-8-325537), guanidine compounds (JP-A-5-271471), benzotriazole-series UV absorbers (JP-A-6-235819), benzophenone-series UV absorbers (JP-A-6-118233), or the like can be used.

(Plasticizer)

The plasticizer that can be used in the present invention is preferably a phosphate and/or a carboxylate. Preferred examples of the phosphate-series plasticizer include triphenyl phosphate (TPP), tricresyl phosphate (TCP), cresyl diphenyl phosphate, octyl diphenyl phosphate, biphenyl diphenyl phosphate (BDP), trioctyl phosphate, and tributyl phosphate. Preferred examples of the carboxylate-series plasticizer include dimethyl phthalate (DMP), diethyl phthalate (DEP), dibutyl phthalate (DBP), dioctyl phthalate (DOP), diphenyl phthalate (DPP), diethyl hexyl phthalate (DEHP), triethyl o-acetylcitrate (OACTE), tributyl o-acetylcitrate (OACTB), triethyl acetyl citrate, tributyl acetyl citrate, butyl oleate, methyl acetyl ricinoleate, dibutyl sebacate, triacetin, tributyrin, butyl-phthalyl-butyl glycolate, ethyl phthalyl ethyl glycolate, methyl phthalyl ethyl glycolate, and butyl-phthalyl-butyl glycolate. Further, the plasticizer is preferably a (di)pentaerylthritol ester, a glycerol ester, or a diglycerol ester.

(Peeling Accelerator)

The peeling accelerator for use when a metal band or drum is used is preferably, for example, ethyl citrate-series.

(Infrared Absorber)

Preferred examples of the infrared absorber include those described in, for example, JP-A-2001-194522.

(Dye)

Further, in the present invention, a dye may be added, to adjust the hue of the resultant film. The amount to be added of the dye is preferably 10 to 1,000 ppm, more preferably 50 to 500 ppm, in terms of ratio by mass to the cellulose acylate. The light piping of the cellulose acylate film can be reduced and the yellowish feel of the cellulose acylate film can be improved, by adding the dye(s) in this manner. The dye may be added together with a cellulose acylate or a solvent, when the cellulose acylate solution is prepared; or alternatively the dye may be added during or after the preparation of the solution. Further, the dye may be added in the ultraviolet absorber solution, which is to be in-line-added. The dyes described in, for example, JP-A-5-34858 may also be used.

(Matting Agent Fine-Particles)

To the cellulose acetate film according to the present invention, fine particles as a matting agent may be added. Examples of the fine particles that can be used in the present invention include silicon dioxide, titanium dioxide, aluminum oxide, zirconium oxide, calcium carbonate, talc, clay, calcined kaolin, calcined calcium silicate, hydrated calcium silicate, aluminum silicate, magnesium silicate, and calcium phosphate. The fine particles are preferably those containing silicon, from the viewpoint of obtaining low turbidity, and particularly silicon dioxide is preferable. Fine particles of silicon dioxide are preferably those having a primary average particle diameter of 20 nm or less and an apparent specific gravity of 70 g/L or more. Particles having a primary average particle diameter as small as 5 to 16 nm are able to reduce the haze of the film, and are hence more preferable. The apparent specific gravity is preferably 90 to 200 g/L, and more preferably 100 to 200 g/L. A larger apparent specific gravity makes it possible to prepare a high concentration dispersion, to thereby better haze and coagulation, which is preferable.

The fine particles generally form secondary particles having an average particle diameter (size) of 0.1 to 3.0 μm; and the fine particles exist in the form of a coagulate of primary particles in the film, to thereby being capable of forming irregularities having 0.1 to 3.0 μm in size on the surface of the film. The secondary average particle diameter is preferably 0.2 μm or more and 1.5 μm or less, more preferably 0.4 μm or more and 1.2 μm or less, and most preferably 0.6 μm or more and 1.1 μm or less. Herein, the primary particle diameter and the secondary particle diameter are determined in the following manner: Particles in the film are observed by a scanning type electron microscope to measure the diameter of a circumscribed circle of a particle as a particle diameter. Further, 200 particles each in a different site or place are observed, to calculate an average of the diameters of these particles to determine an average particle diameter.

As the fine particles of silicon dioxide, for example, commercially available products under such trade names as Aerosil R972, R972V, R974, R812, 200, 200V, 300, R202, 0X50, TT600 (manufactured by Nippon Aerosil Co., Ltd.) may be used. The fine particles of zirconium oxide are commercially available, for example, under such trade names as Aerosil R976 and R811 (manufactured by Nippon Aerosil Co., Ltd.), which may be used in the present invention.

Of those fine particles, Aerosil 200V and Aerosil R972V are particularly preferable, since they are fine particles of silicon dioxide having an average primary particle diameter of 20 nm or less and an apparent specific gravity of 70 g/L, or more, and having a large effect of dropping friction coefficient, while maintaining the low turbidity of a resulting optical film.

In the present invention, to obtain a cellulose acylate film containing particles having a small secondary average particle diameter, several methods can be applied in the process of preparing a dispersion of fine particles. For example, in one method, a fine-particle dispersion obtained by mixing and stirring a solvent and fine particles, is prepared in advance. This fine particle dispersion is added into a small amount of a cellulose acylate solution which is separately prepared, and the mixture is dissolved with stirring. Then, the obtained mixture is further mixed in a main cellulose acylate dope solution. This method is a preferable preparation method in the point that the silicon dioxide fine-particles are well dispersed and are scarcely re-coagulated. Besides the above method, there is a method in which a small amount of a cellulose ester is added to a solvent, dissolved with stirring, fine particles are added thereto, and followed by dispersing by a dispersing apparatus, to obtain a fine-particle addition solution, which is sufficiently mixed with a dope solution by using an inline mixer. The present invention is not particularly limited by those methods, but the concentration of silicon dioxide when silicon dioxide fine-particles are mixed with and dispersed in, for example, a solvent is preferably 5 to 30 mass %, more preferably 10 to 25 mass %, and most preferably 15 to 20 mass %. The higher the concentration of the dispersion is, the lower the liquid turbidity in relation to the amount to be added is and the more greatly the haze and coagulate are bettered, and thus a higher concentration of silicon dioxide is preferable. The amount of the matting agent to be added in the final dope solution of the cellulose acylate is preferably 0.01 to 1.0 $g/m^2$, more preferably 0.03 to 0.3 $g/m^2$, and most preferably 0.08 to 0.16 g/m.

Preferable examples of a lower alcohol to be used as the solvent include methyl alcohol, ethyl alcohol, propyl alcohol, isopropyl alcohol, and butyl alcohol As the solvent other than the lower alcohol, a solvent which is usually used for forming a cellulose ester film is preferably used, though not particularly limited to these solvents.

[Producing Process of Cellulose Acylate Film]

The cellulose acylate film according to the present invention is preferably produced by solvent casting method. For reduction of the dispersion of the Re and Rth, the concentration of the cellulose acylate solution is preferably 16 mass % to 30 mass %, more preferably 18 mass % to 26 mass %. The organic solvent used is not particularly limited, but a mixture of solvents selected from chlorine-based solvents, alcohols, ketones, and esters is favorably used. The chlorine-based solvent is preferably methylene dichloride or chloroform. Alcohols favorably used include methanol, ethanol, 1-propanol, 2-propanol, and 1-butanol; esters favorably used include methyl acetate; and ketones favorably used include acetone and cyclopentanone, and particularly favorably used is cyclohexanone.

In preparing the cellulose acylate solution, the cellulose acylate is first added to and swollen in a solvent placed in a tank at room temperature, while the solution is agitated. A swelling period of 10 minutes or more, which leads to complete dissolution without any undissolved residue, is preferable. In addition, the solvent temperature is preferably 0 to 40° C. A temperature of 0° C. or higher is preferable for favorable swelling speed and complete dissolution without undissolved residue, and a temperature of 40° C. or lower is preferable for sufficient swelling of the central region without unfavorable drastic swelling. The cellulose acylate may be dissolved by cold dissolution method or hot dissolution method, or alternatively in combination of these. Any one of known methods such as those described in Japan Institute of Invention and Innovation, Kokai Giho (Open Technical Report) 2001-1745 may be used for cold or hot dissolution method. Alternately, the cellulose acylate solution thus obtained may be preferably prepared by first forming a low concentration solution and then concentrating it to a suitable concentration by concentration means.

A dissolution method favorably used in the present invention is, for example, dissolution under high pressure aid high temperature. As described in JP-A-5-163301, it is a method of adding a cellulose acylate into a solvent, agitating the mixture at 10 to 35° C. under normal pressure for 20 to 180 minutes, feeding the solution by gear pump to a heat exchanger, heating the solution therein under pressure at 60° C. or higher for complete dissolution, and cooling the solution to room temperature additionally in a cooling heat exchanger. The heating temperature is preferably 60 to 120° C., still more preferably 70 to 100° C. At that time, a pressure, which corresponds to the solvent's vapor pressure at the dissolution temperature, is applied to the solution. The heating period is at least 1 minute or more, preferably 5 minutes to 6 hours, more preferably 10 minutes to 3 hours. The concentration of the cellulose acylate in solution is preferably 15 to 24 mass %, more preferably 16 to 22 mass %. Unfavorably, higher concentration makes dissolution more difficult, while lower concentration leads to low viscosity, which makes casting more difficult and demands additional operation for concentration.

Any one of solution-casting methods and devices traditionally used for production of cellulose triacetate film may be used as the method and the facility for casting the cellulose acylate film according to the present invention. A dope (cellulose acylate solution) previously prepared in a dissolution tank is stored once in a stock tank, for final adjustment of the dope by removal of the bubbles contained therein. The resulting dope is supplied from a dope outlet port by a high-pressure quantitative gear pump allowing high-precision quantitative feeding to a high-pressure die; the dope is cast uniformly out of the head (slit) of the high-pressure die onto a metal support (band or drum) running endlessly in the casting region; and the half dried dope film (referred to as web) is separated from the metal support. The web obtained is conveyed in a tenter while both ends thereof in the width direction are held with clips or pin tenters, stretched or contracted as needed in the width direction and dried, and then, further conveyed by rolls in a dryer, to complete drying, and finally, wound by a winding machine to a roll having a particular length of film. The combination of the tenter and rolls with the dryer, the temperatures thereof, and the residual solvent contents at respective points may be altered according to its application.

In production of the cellulose acylate film according to the present invention, the dope applied on a metal substrate is dried preferably at a temperature of 30 to 250° C., more preferably 40 to 180° C., and most preferably 40 to 140° C. The drying is preferably performed in some divided zones different in temperature.

The thickness of the cellulose acylate film obtained (after drying) in the present invention is preferably in the range of 30 to 100 µm, more preferably in the range of 40 to 80 µm. A film having a desired thickness can be formed by adjusting the solid matter concentration in dope, the clearance of die head slit, the extruding flow rate from die, the pressure, the traveling speed of the metal support, and others.

The width of the cellulose acylate film thus obtained is preferably 0.5 to 3 m, more preferably 0.6 to 2.5 in, and more preferably 0.8 to 2.2 in. The winding length per roll is preferably 100 to 10,000 m, more preferably 500 to 7,000 m, and still more preferably 1,000 to 6,000 m. During winding, at least one edge of the film is preferably knurled, and the knurling width is preferably 3 mm to 50 mm, more preferably 5 mm to 30 mm, and the knurling height is preferably 0.5 to 500 µm, more preferably 1 to 200 µm. The film may be knurled only on one side or on both sides.

[Optical Properties of Cellulose Acylate Film]

The optical anisotropy in the present invention is a parameter determined by the retardations in the in-plane and thickness directions of the film described above, and "smaller optical anisotropy" means "smaller retardation value".

The cellulose acylate film according to the present invention has smaller optical anisotropy, with the Re value of 0 nm or more and 20 nm or less at a wavelength of 590 nm and the Rth value of −10 nm or more and 15 nm or less at a wavelength of 590 mn, and smaller wavelength dispersion with a difference in the Rth value between those at wavelengths 480 nm and 630 nm, |Rth(630)−Rth(480)|, of 20 nm or less.

[Application (Optical Compensation Film)]

The cellulose acylate film according to the present invention is preferably used particularly in IPS-type liquid crystal display devices. The cellulose acylate film can reduce the light leakage and the color change by view angle, caused by the difference between the direction of the polarized light passing through the light source-side polarizing plate and the direction of the absorption axis of the front-side polarizing plate when seen at an inclined angle.

The cellulose acylate film according to the present invention, which does not show unneeded anisotropy and expresses only the optical properties of optical anisotropic layer when used in combination with a birefringent optical anisotropic layer, is particularly effective when used as an optical compensation film of liquid crystal display devices. The optical compensation film is an optical material commonly used in liquid crystal display devices and used for compensating phase difference, and is identical with phase difference plate, optical compensation sheet or the like. The optical compensation film, which is birefringent, is used for prevention of coloration of liquid crystal display devices and improvement of view angle characteristics.

The optical anisotropic layer of the optical compensation film is formed with a liquid crystalline compound or a polymer film. The liquid crystalline compound is preferably a discotic or rod-shaped liquid crystalline compound.

(Discotic Liquid Crystalline Compound)

Examples of the discotic liquid crystalline compound for use in the present invention include compounds described in various references (C. Destrade et al., Mol. Crysr. Liq. Cryst., vol. 71, p. 111 (1981); the Chemical Society of Japan Ed., Quarterly Chemical Review, No. 22, Chemistry of liquid crystals, Chapter 5 and Chapter 10 Section 2, (1994); B. Kohne et al., Angew. Chem. Soc. Chem. Comm., page 1794 (1985); J. Zhang et al., J. Am. Chem. Soc., vol. 116, page 2655 (1994)).

The discotic liquid crystalline molecule is preferably immobilized in the oriented state in the optical anisotropic layer, most preferably it is immobilized by polymerization reaction. Polymerization of the discotic liquid crystalline molecule is described in JP-A-8-27284. For immobilization of the discotic liquid crystalline molecule by polymerization, a polymerizable group should be bound to the disk-shaped core of the discotic liquid crystalline molecule as a substituent. However, direct binding of the polymerizable group to the disk-shaped core makes it difficult to preserve the orientation state during polymerization reaction. For that reason, a connecting group is introduced to the site between the disk-shaped core and the polymerizable group. The polymerizable group-containing discotic liquid crystalline molecules are disclosed in JP-A-2001-4387.

(Rod-Shaped Liquid Crystalline Compound)

Examples of the rod-shaped liquid crystalline compound which can be used in the present invention include azomethines, azoxys, cyanobiphenyls, cyanophenyl esters, benzoic esters, cyclohexanecarboxylic phenyl esters, cyanophenylcyclohexanes, cyano-substituted phenylpyrimidines, alkoxy-substituted phenylpyrimidines, phenyldioxanes, tolans, and alkenylcyclohexylbenzonitriles. In addition to the foregoing low-molecular weight liquid crystalline compounds, polymeric liquid crystalline compounds can also be used.

In the optical anisotropic layer, the rod-shaped crystalline molecule is preferably immobilized in the oriented state, most preferably immobilized by polymerization reaction. Examples of the polymerizable rod-shaped liquid crystalline compounds which can be used in the present invention include the compounds described in Makromol. Chem., vol. 190, p. 2255 (1989), Advanced Materials vol. 5, p. 107 (1993), U.S. Pat. Nos. 4,683,327, 5,622,648, 5,770,107, International Patent (WO) Nos. 95/22586, 95/24455, 97/00600, 98/23580 and 98/52905, JP-A-1-272551, JP-A-6-16616, JP-A-7-110469, JP-A-11-80081, and JP-A-2001-328973, and others.

(Optical Anisotropic Layer Formed of Polymer Film)

A polymer film forming the optical anisotropic layer is preferably produced by a method of using at least one polymer material selected from the group consisting of polyamide, polyimide, polyester, polyether ketone, polyamide-imide, polyester-imide, and polyarylether ketone, dissolving it in a solvent, coating the solution on a base material of the cellulose acylate film according to the present invention, and forming a dry film by vaporization of the solvent. In this process, it is also preferable to stretch the polymer film and the base material for expression of optical anisotropy and use the resultant as an optical anisotropic layer, and the cellulose acylate film according to the present invention can be used favorably as the base material. Alternatively, the polymer film may be formed on a separate base material, peeled off from the base material, and bonded to the cellulose acylate film according to the present invention, for use as an optical anisotropic layer. It is possible to thin the polymer film by this method, and the thickness is preferably 50 μm or less, more preferably 1 to 20 μm.

[Functional Layers]

(Hard-Coat Film, Anti-Glare Film, and Anti-Reflection Film)

In particular because transparent hardcoat layer, anti-glare layer, anti-reflection layer, and others are formed on the polarizing plate-protecting film of the display-side outmost layer of liquid crystal display devices, the polarizing plate-protecting film is particularly favorably used in the portion.

The cellulose acylate film according to the present invention can also be used favorably as a hard-coat film, an anti-glare film, an anti-reflection film, or an antistatic film. For improvement in visibility of flat panel display devices such as LCD, PDP, CRT, and EL, at least one or all of a hardcoat layer, an anti-glare layer, an anti-reflection layer, and a conductive layer may be formed on one face or both faces of the cellulose acylate film according to the present invention. Favorable examples of the anti-glare and anti-reflection films are described in detail in Japan Institute of Invention and Innovation, Kokai Giho (JTD No. 2001-1745, pp. 54 to 57, Mar. 15, 2001, Japan Institute of Invention and Innovation), and the cellulose acylate film according to the present invention may be used favorably.

[Application (Polarizing Plate)]

The cellulose acylate film according to the present invention is useful particularly as a polarizing plate-protecting film. When it is used as a polarizing plate-protecting film, the method of producing the polarizing plate is not particularly limited, and it may be produced by a common method. For examples, it is produced by treating the cellulose acylate film obtained with alkali and bonding the film to both faces of a polarization film, which is previously prepared by wet stretching of a polyvinylalcohol film in an iodine solution, with an adhesive of aqueous completely saponified polyvinylalcohol solution. The film may be treated by easier bonding processing, instead of the alkali treatment, as described in JP-A-6-94915 and JP-A-6-118232.

Examples of the adhesives used in bonding the treated face of the protective film and the polarization film to each other include polyvinylalcohol-based adhesives such as polyvinylalcohol and polyvinylbutyral, vinyl-based latexes such as butyl acrylate.

The polarizing plate consists of a polarization film and protective films protecting both faces thereof, and a protection film may further be formed on one face of the polarizing plate and a separate film on the other face. The protection film and the separate film are used for protection of the polarizing plate, for example, during shipment and product inspection of the polarizing plate. In such a case, the protection film is bonded for protection of the polarizing plate, and thus, to the face of the polarizing plate opposite to the face to be bonded to the liquid crystal plate. The separate film is used for covering the adhesive layer to be bonded to the liquid crystal plate, and bonded to the face of the polarizing plate to be bonded to the liquid crystal plate.

(Kinds of Liquid Crystal Display Devices)

The cellulose acylate film of the present invention can be applied to liquid crystal cells of various display modes. Specifically, as for the display modes, proposed are various modes, for example, TN (Twisted Nematic), IPS (In-Plane Switching), FLC (Ferroelectric Liquid Crystal), AFLC (Anti-ferroelectric Liquid Crystal), OCB (Optically Compensatory Bend), STN (Supper Twisted Nematic), VA (Vertically Aligned), ECB (Electrically Controlled Birefringence), and HAN (Hybrid Aligned Nematic). It can also be used in a display mode in combination of the display modes as they are divided in an orientation. The cellulose acylate film according to the present invention can also be used favorably in any liquid crystal display device, such as transmission-type, reflection-type, or semi-transmission-type liquid crystal display device.

<Photographic Film Support>

The cellulose film of the present invention may be applied as a support of a silver halide photographic photosensitive material. Specifically, in accordance with the techniques concerning color negatives described in JP-A-2000-105445, the cellulose film of the present invention can be preferably used in the aforementioned color negatives. Further, the cellulose film is also preferably applied as the support of a color reversal silver halide photographic photosensitive material, and in accordance with various raw materials, formulations, and processing or treating methods, as described in JP-A-11-282119, it can be prepared.

<Transparent Substrate>

Since the cellulose film of the present invention is close to zero in the optical anisotropy and can have excellent transparency, the cellulose acylate film may be used in place of a liquid crystal cell glass substrate of a liquid crystal display, i.e. it may be used as a transparent substrate that seals a driving liquid crystal.

Because it is necessary that the transparent substrate that seals a liquid crystal be excellent in gas barrier properties, the cellulose film of the present invention may be provided with a gas barrier layer on the surface thereof, if necessary. There is no particular limitation on the shape and material of the gas barrier layer. Specifically, any of the following methods may be given, in which, on at least one of the surfaces of the cellulose film of the present invention, $SiO_2$ or the like is vapor-deposited, or a coating layer of a polymer, such as a vinylidene chloride-series polymer or vinyl alcohol-series polymer, which is relatively high in gas barrier properties, is formed. Any of these methods may be appropriately used in the present invention.

Further, when the cellulose film is used as a transparent substrate that seals a liquid crystal, it may be provided with a transparent electrode(s) to drive the liquid crystal by applying voltage. There is no particular limitation on the transparent electrode, but a metal film, metal oxide film or the like may be laminated, to thereby form the transparent electrode(s), on at least one of the surfaces of the cellulose film of the present invention. Of those, a film of a metal oxide is preferable, from the viewpoints of transparency, electrical conductivity, and mechanical characteristics. In particular, a thin film of indium oxide containing tin oxide primarily and 2 to 15% of zinc oxide, can be preferably used. The details of these techniques described in, for example, JP-A-2001-125079 and JP-A-2000-227603 can be used.

The present invention provides a cellulose-film modifier that is resistant to thermal volatilization and excellent in dope stability and gives a cellulose film lower in optical anisotropy.

The present invention also provides a cellulose composition containing the cellulose modifier and a cellulose film lower in optical anisotropy prepared by using the same.

The present invention further provides a polarizing plate-protecting film, a polarizing plate, a liquid crystal display device, and a substrate for silver halide photographic photosensitive material prepared by using the cellulose film lower in optical anisotropy.

The cellulose-film modifier according to the present invention, which is resistant to thermal volatilization or precipitation during casting and drying of the film and also to leaching into the saponification liquid, reduces the optical anisotropy of the cellulose film, as it is added to the cellulose compound. The cellulose film according to the present invention can be used favorably, for example, as a polarizing plate-protecting film, a polarizing plate, a liquid crystal display device, a silver halide photographic photosensitive material, or the like.

The present invention will be described in more detail with the following examples. The materials, the amounts to be used, the proportions, the contents and procedures of treatment or processing, which will be shown in the examples, may be appropriately changed or modified, without departing from the spirit of the present invention. Therefore, the following examples are not interpreted as limiting of the scope of the present invention.

EXAMPLES

Synthetic Example 1

96 g of citric acid, 158.4 g of 3-pentanol, and 500 ml of toluene were placed in a 1,000-ml three-necked flask equipped with a mechanical stirrer, a thermometer, a Dean-Stark tube, a condenser tube and a dropping fuel, and the mixture was agitated at room temperature, to give a mixture solution. 5 ml of conc. sulfuric acid was added dropwise gradually into the mixture solution, and the mixture solution was heated under reflux, and reacted until no water was distilled. 25 g of calcium carbonate was added to the residue liquid, and the reaction system was condensed as it was by using an aspirator, to give an oily product. The oily product obtained was dissolved in 1,000 ml of ethyl acetate; the solution was washed with 1,000 ml of water and 1,000 ml of saturated sodium bicarbonate water respectively twice, and the organic layer obtained was dried over magnesium sulfate. After removal of magnesium sulfate by filtration, the organic layer was concentrated in an evaporator, and dried under vacuum at room temperature, to give 180.9 g of a desired compound A-1 (yield: 93%). The compound was identified as A-1 by $^1$H-NMR measurement.

Compounds A-2, A-4 and A-6 and a comparative compound C-1 were prepared and identified similarly, while 3-pentanol was replaced with each alcohol.

Synthetic Example 2

Synthesis of A-12

44.4 g of A-6 obtained in Synthetic Example 1 described above, 150 ml of toluene, and 0.1 ml of conc. sulfuric acid were placed in a 300-ml three-necked flask equipped with a mechanical stirrer, a thermometer, a Dean-Stark tube, a condenser tube and a dropping funnel, and the mixture was agitate at room temperature, to give a mixture solution. While the solution was cooled with water, 20.4 g of acetic anhydride was added dropwise to the mixture solution gradually with taking care that the reaction temperature would be kept not higher than 100° C., and then the mixture solution was allowed to react at 100° C. for 2 hours. 10 g of calcium carbonate was added to the residue liquid, and the reaction system was concentrated as it was by using an aspirator, to give an oily product. The oily product obtained was dissolved in 300 ml of ethyl acetate, and the ethyl acetate solution was washed with 300 ml of water and 300 ml of 1 N aqueous hydrochloric acid and 300 ml of saturated sodium bicarbonate water respectively twice, and the organic layer obtained was dried over magnesium sulfate After separation of magnesium sulfate by filtration, the organic layer was concentrated in the evaporator and dried under vacuum at room temperature, to give 45.0 g of a desired compound A-13 (yield: 98%). The compound was identified as A-12 by $^1$H-NMR measurement.

Example 1

(Preparation of Cellulose Acetate Solution)

The following compositions containing the cellulose acetates different in acetyl substitution degree and molecular weight as shown in Table 2, which were prepared by changing the condition during acetyl substitution such as catalyst amount, reaction concentration, reaction temperature, and reaction time, were each placed in a mixing tank and agitated for dissolution of respective components, to give a cellulose acetate solution.

| (Composition of cellulose acetate solution) | |
|---|---|
| Cellulose acetate (Substitution degree: 2.92, GPC weight-average molecular weight: 250,000) | 100.0 mass parts |
| Methylene chloride (First solvent) | 348.0 mass parts |
| Methanol (Second solvent) | 52.0 mass parts |

The compound capable of lowering optical anisotropy, the wavelength dispersion adjustor and others shown in the following Table 2 were mixed in the addition amounts shown in Table 2 and fed into a mixing tank; the mixture was agitated for dissolution of respective components, mixed with one of the cellulose acetate solution above, and adjusted to a solid matter concentration of 20 mass %, to give a dope.

[Compound Volatilization After Heat Treatment of Film]

The degree of volatilization from the film can be determined by dissolving a film treated at 150° C. for 10 hours and an untreated film respectively in solvents, detecting the compounds by high-speed liquid chromatography, assuming that the compound peak area observed corresponds to the amount of the compound remaining in the film, and calculating according to the following Formula:

Volatilization (%)={(Compound remaining in untreated sample)−(Compound remaining in treated sample)}/(Compound remaining in untreated sample)×100

[Measurement of Film Optical Properties]

$Re(\lambda)$ and $Rth(\lambda)$ at a wavelength of $\lambda$ were determined by using KOBRA 21WR (manufactured by Oji Scientific Instruments Co., Ltd.) after the sample film was left in measurement environment for one hour.

<Evaluation of Cellulose Acetate Film>

The volatilization, and the Rth of the cellulose acetate film obtained were evaluated. In the present Example, these tests were performed similarly to the, [volatilization amount of compound after heat treatment of film], and [measurement of film optical properties] described above.

TABLE 2

| Example | Compound/Addition amount | | Wavelength dispersion adjustor/Addition amount | | Dope stability | Volatilization amount of compound | Rth(590) | Rth(630)-Rth(480) |
|---|---|---|---|---|---|---|---|---|
| Sample 1 | A-1 | 12 | triazine* | 1.2 | 98 | 0.3 | −8 | 15 |
| Sample 2 | A-2 | 12 | triazine* | 1.2 | 99 | 0.2 | −6 | 14 |
| Sample 3 | A-3 | 12 | triazine* | 1.2 | 100 | 0.1 | −7 | 16 |
| Sample 4 | A-5 | 6 | triazine* | 1.2 | 100 | 0.1 | −2 | 13 |
| Sample 5 | A-5 | 12 | triazine* | 1.2 | 99 | 0.1 | −6 | 12 |
| Sample 6 | A-5 | 12 | triazine* | 2.2 | 99 | 0.1 | 0 | 8 |
| Sample 7 | A-5 | 12 | triazine* | 0.6 | 99 | 0.1 | −10 | 20 |
| Sample 8 | A-5 | 18 | triazine* | 1.2 | 98 | 0.2 | −10 | 12 |
| Sample 9 | TPP/BDP | 8/4 | triazine* | 1.2 | 95 | 8.1 | 30 | 20 |
| Sample 10 | C-1 | 12 | triazine* | 1.2 | 90 | 6.9 | 0 | 15 |
| Sample 11 | C-1 | 12 | triazine* | 1.2 | 90 | 0.2 | −4 | 15 |
| Sample 12 | C-2 | 12 | triazine* | 1.2 | 88 | 0.1 | −2 | 15 |

(Note)
The addition amount is a rate (mass %) with respect to the mass of the cellulose acetate.
Wavelength dispersion adjustor compound (triazine*)

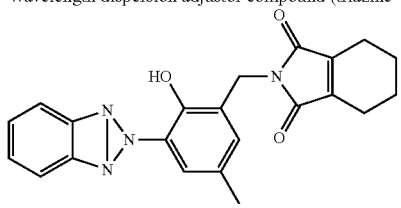

[Stability of Additives During Dissolution by Heating]

Each of the dopes having the composition shown in Table 2 was placed and sealed in a pressure container and heated at 95° C. for 1 hour, and decomposition of the additives in the dope after cooling was evaluated by gas chromatography.

Stability (%)=Additive content after heating/Additive content in untreated dope×100

[Preparation of Transparent Film by Using Cellulose Acetate Dope]

The cellulose acetate dopes were each filtered and coated by using a band casting machine. The films were peeled off from the band at a residual solvent amount of 30%, stretched in a tenter, dried at 135° C. to a residual solvent content of 0.2 mass % or less, cooled, and wound, to give each of transparent film samples 1 to 8 of the present invention and comparison samples 9 and 10.

The structures of the comparative compounds TPP, BDP, C-1 and C-2 shown in Table 2 are shown below:

Comparative compounds

TPP/BDP

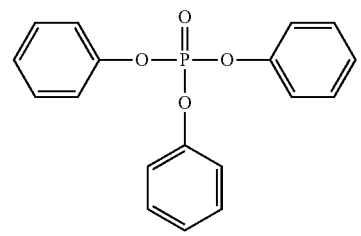

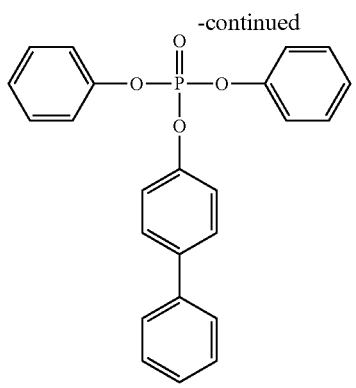

C-1

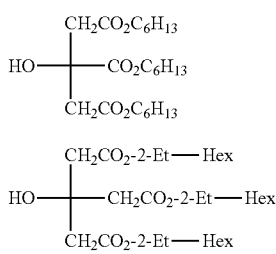

C-2

Ex: ethyl group, Hex: hexyl group

The results in Table 2 indicated that it was possible to produce a cellulose acetate film significantly better in dope stability, lower in volatility and smaller in optical anisotropy (Rth) by addition of the compound A-1, A-2, A-3, or A-5 according to the present invention than by addition of commonly used TPP/BDP or the compound C-1 or C-2 having a skeleton similar to that of the modifier of the present invention (outside the scope of the provision of the present invention).

Example 2

A polarizing plate and a liquid crystal display device were prepared by using the sample 5, 7 or 9 as the protective film (FIG. 1). Specifically, a top polarizing plate (protective film: H1, polarizer: P1, protective film: A1), a liquid crystal cell (phase difference film A: L1, liquid crystal layer: L2, phase difference film B: L3), a bottom polarizing plate (protective film: A2, polarizer: P2, protective film: H2) were laminated in that order from the observation direction (top), and a backlight source (not shown in the Figure) was connected thereto.
<Protective Films H1 and H2>

A commercially available cellulose acetate film (Fujitac TD80UF, manufactured by Fuji Photo Film Co., Ltd.) was used as the protective films H1 and H2.
<Polarized Film>

A polarized film of the stretched polyvinylalcohol film with adsorbed iodine was prepared and used.
(Preparation of Polarizing Plate)

Each of the transparent film samples 5, 7 and 9 was immersed in 1.5 N aqueous sodium hydroxide solution at 55° C. for 2 minutes, washed in a water-washing bath at room temperature, and neutralized at 30° C. by using 0.1 N sulfuric acid. The sample was washed once again in a water-washing bath at room temperature and dried in hot air at 100° C.

Subsequently, a roll-shaped polyvinylalcohol film having a thickness of 80 μm was stretched five times continuously in an aqueous iodine solution and dried, to give a polarization film having a thickness of 20 μm. The polarization film was bonded to the alkali-saponified transparent film sample and the protective film with the polarization film held inside, by using 3% aqueous polyvinylalcohol (PVA-117H by Kuraray) solution as an adhesive, to give a polarizing plate. The optical properties of the polarizing plate obtained by using the cellulose acylate film of the invention were excellent. There was also no particular problem in durability over time.
<Preparation of IPS Mode Liquid Crystal Cell>

Electrodes were formed on a glass plate at an inter-electrode distance of 20 μm, and an oriented polyimide film was formed thereon and subjected to rubbing treatment. A polyimide film was formed on one surface of a glass plate separately prepared and oriented (aligned) by rubbing treatment. The two glass plates were imposed on each other at a substrate gap ($d_1$) of 3.9 μm with the orientation films facing each other and with the rubbing directions of the two glass plates in parallel, and then, a nematic liquid crystal composition having a refractive index anisotropy (Δn) of 0.0769 and a dielectric anisotropy (Δ∈) of plus 4.5 was sealed therein. The $d_1 \cdot \Delta n$ value of the liquid crystal layer was 300 nm.
(Crystal Display Device)

The polarizing plate prepared was bonded to both faces of the IPS-mode liquid crystal cell with an adhesive, with the film according to the present invention faced the liquid crystal cell. The polarizing plate at the viewer side was layered, so that the absorption axis of the polarizing plate was aligned in the direction perpendicular to the abnormal light refractive index direction of the liquid crystal composition in the liquid crystal cell when no voltage was applied. Further, the absorption axis of the backlight-side polarizing plate was placed in the direction perpendicular to the absorption axis of the viewer-side polarizing plate.
(Evaluation)

The light leakage from the IPS panel under black display in the direction at an inclination angle of 45° and the change in color tone were observed. Display devices which used sample 5 or 7 as the protective film A1 were obviously smaller in light leakage and in color change as seen from the inclined angle than the display devices which used sample 9 or a common Fujitac TD80UF polarized light plate. It is a synergic effect of the small Re and Rth values of the protective film.

Having described our invention as related to the present embodiments, it is our intention that the invention not be limited by any of the details of the description, unless otherwise specified, but rather be construed broadly within its spirit and scope as set out in the accompanying claims.

What we claim is:

1. A cellulose-film modifier, comprising a compound represented by the following Formula (3):

Formula (3)

$R^{21}$ represents a hydrogen atom or an aliphatic acyl group; $R^{22}$, $R^{23}$ and $R^{24}$ each represent a substituent selected from the group consisting of 1-ethylpropyl, 1-ethylbutyl, 1-propylbutyl, 1-methyl-3-butenyl, 1-methylhexyl, 1-phenylheptyl, 1-methylpropyl, 1-methylnonenyl, a substituent represented by the following Formula:

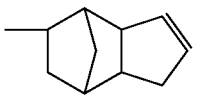

and a substituent represented by the following Formula:

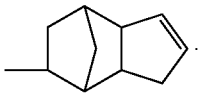

2. A cellulose composition, comprising a cellulose compound and at least one cellulose-film modifier described in claim 1.

3. An optical cellulose film, wherein at least one cellulose-film modifier described in claim 1 is contained in a cellulose compound.

4. The optical cellulose film described in claim 3, wherein the cellulose compound contained in the cellulose film is a cellulose acylate.

5. The optical cellulose film described in claim 4, wherein the acyl substitution degree of the cellulose acylate is 2.60 to 3.00.

6. The optical cellulose film described in claim 3, wherein the substitution degree of acyl groups having 3 to 22 carbon atoms in the cellulose acylate is 0.00 to 0.80.

7. The optical cellulose film described in claim 3, wherein Re value at a wavelength of 590 nm is 0 nm or more and 20 nm or less, and Rth value at a wavelength of 590 nm is −10 nm or more and 15 nm or less.

8. The optical cellulose film described in claim 3, wherein the Rth values at wavelengths of 480 nm and 630 nm satisfy the relationship shown by the following mathematical formula (1):

$$|Rth(630)-Rth(480)| \leq 20 \qquad \text{Mathematical formula (1).}$$

9. The optical cellulose film described in claim 3, containing the cellulose compound and at least one compound represented by the Formula (3) in an amount of 2 to 30 mass % of the cellulose compound.

10. A polarizing plate-protecting film, comprising the optical cellulose film described in claim 3.

11. A polarizing plate, comprising a polarization film and two transparent protective films placed on both sides of the polarization film, wherein at least one of the transparent protective films is the polarizing plate-protecting film described in claim 10.

12. A liquid crystal display device comprising a liquid crystal cell and two polarizing plates placed on both sides of the liquid crystal cell, wherein at least one of the polarizing plates is the polarizing plate described in claim 11.

* * * * *